US005496399A

United States Patent [19]

Ison et al.

[11] Patent Number: 5,496,399
[45] Date of Patent: Mar. 5, 1996

[54] STORAGE STABLE CALCIUM PHOSPHATE CEMENTS

[75] Inventors: Ira C. Ison, Campbell; Mark T. Fulmer; Bryan M. Barr, both of San Jose; Brent R. Constantz, Los Gatos, all of Calif.

[73] Assignee: Norian Corporation, Mountain View, Calif.

[21] Appl. No.: 294,325

[22] Filed: Aug. 23, 1994

[51] Int. Cl.$^6$ ..................................................... C04B 12/02
[52] U.S. Cl. .......................... 106/35; 106/690; 423/305; 423/308; 423/309; 423/311; 433/199.1
[58] Field of Search ............................. 106/35, 690, 691; 423/305, 308, 309, 311, 313; 433/199.1; 623/16, 901

[56] References Cited

U.S. PATENT DOCUMENTS

| | | | |
|---|---|---|---|
| Re. 33,161 | 2/1990 | Brown et al. | 423/308 |
| Re. 33,221 | 5/1990 | Brown et al. | 423/308 |
| 4,880,610 | 11/1989 | Constantz | 423/305 |
| 5,053,212 | 10/1991 | Constantz et al. | 423/305 |
| 5,129,905 | 7/1992 | Constantz | 606/76 |
| 5,178,845 | 1/1993 | Constantz et al. | 423/305 |

OTHER PUBLICATIONS

TenHuisen & Brown, "The formation of Hydroxyapatite–Gelatin Composites at 38° C.," J. Biomedical Materials Research (1994) 28: 27–33.
Lerner & Azoury, "Rapid Precipitation of Apatite from Ethanol–Water Solution," J. Crystal Growth (1989) 97: 725–730.
Yoshimura & Suda, "Hydrothermal Processing of Hydroxyapatite: Past, Present, and Future," in Hydroxyapatite and Related Materials, p. 72 (1993).
TenHuisen, "The Formation of Biocomposites at Physiological Temperature," Thesis, The Pennsylvania State University, (Aug. 1992).
"Calcium Phosphate Cements: Effect of Fluorides on the Setting & Hardening of β–Tricalcium Phosphate–Dicalcium Phosphate–Calcite Cements" Mirtchi et al. Biomaterials (1991) vol. 12 pp. 505–510.
"Calcium Phosphate Cements: Study of the β–Tricalcium Phosphate–Monocalcium Phosphate System" Mirtchi et al. Biomaterials (1989) vol. 10 pp. 475–480.
"Calcium Phosphate Materials: Reactor Response" Reprint from Advances in Dental Research, (Aug. 1989) Chow pp. 181–184.
"Setting Reactions and Compressive Strengths of Calcium Phosphate Cements" Fukase et al. (Reprint from Journal of Dental Research) (Dec. 1990) pp. 1852–1856.
"Calcium Phosphate Cements: Study of the β–Tricalcium Phosphate–Dicalcium Phosphate–Calcite Cements" Mirtchi et al., Biomaterials (1990), vol. 11, pp. 83–88.
The Centennial Memorial Issue of the Ceramic Society of Japan–"Development of Self Setting Calcium Phosphate Cements" Chow (from Journal of the Ceramic Society of Japan) vol. 99 [10] (1991) pp. 954–964.

Primary Examiner—Paul Marcantoni
Attorney, Agent, or Firm—Bertram I. Rowland; Bret E. Field

[57] ABSTRACT

Two component, storage stable apatitic cement compositions, as well as methods for their production, are provided. The dry component of subject apatitic cements comprises basic calcium source particles at least partially coated with a partially neutralized acidic calcium phosphate. The dry component of subject compositions is prepared by combining basic calcium source particles with dissolved acidic phosphate in at least a partially aqueous medium, whereby the basic calcium source particles become partially coated with a partially neutralized acidic calcium phosphate. The reaction is terminated prior to completion of the reaction between the acidic phosphate and the basic calcium source by removing the available water from the reaction mixture. In a first mode, the subject cement may be produced by mechanically mixing an acidic phosphate source with basic calcium source particles in the presence of an aqueous solvent and stopping the reaction between the acid and base prior to completion. Alternatively, a phosphoric acid solution may be rapidly combined with a basic calcium phosphate particle slurry such that partially neutralized acidic calcium phosphate precipitates on the surface of the basic calcium phosphate particles.

7 Claims, No Drawings

STORAGE STABLE CALCIUM PHOSPHATE CEMENTS

INTRODUCTION

1. Technical Field

The technical field of this invention is calcium phosphate cements.

2. Background

In an effort to provide the health care industry with bone substitute materials for the treatment of broken or deteriorating bone, a variety of compositions have been developed. When using bone substitute materials, a physician will typically remove the broken or deteriorated portion of the natural bone and replace it with the bone substitute material.

Cement compositions that currently find use in bone repair include those cements based on polymethylmethacrylate (PMMA) and those based on calcium phosphate minerals. Although PMMA cements have been used with success, cements based on calcium phosphates, i.e. apatitic cements tend to be more biocompatible and more closely resemble the natural mineral structure of bone. For example, hydroxyapatite is a popular bone substitute material because of its close chemical and/or structural resemblance to natural bone.

Calcium phosphate cements, also known as apatitic cements, generally are produced from an acidic source and a basic source. Currently, apatitic cements are available in either three component or two component forms. In three component apatitic cements, an acidic source is kept separate from a basic source, as well as the third component which is a lubricant, until the cement is to be used, e.g. during a bone repair operation. When the cement is to be used, the user, e.g. a physician or nurse, first mixes the acidic source with the basic source. The user then mixes the combined sources with a lubricant to obtain a moldable paste. The moldable paste is then applied to the bone site, where it sets into a solid, bone-like structure. Although three component cements are advantageous in that they are storage stable and have a long shelf life, the need to perform a two step mixing process has disadvantages. A two step mixing process adds to the complexity of, as well as the time required for, the overall treatment procedure.

In an effort to address the disadvantages found in three component cements, two component apatitic cement compositions have been developed. In these two component cements, the acidic and basic sources are provided to the user premixed as a single dry component. To use the cement, the user combines this dry component with the lubricant in a single mixing step. Although using two component cements requires one step mixing, the cements tend to be less stable than their three component counterparts. Since the acidic and basic sources are not separate in the dry component of the two component cement compositions, a slow reaction between the two sources may occur even though the cement has not been combined with a lubricant. This slow reaction between the two sources adversely affects the stability of the cements and makes storage for extended periods of time difficult.

Thus, there is significant interest in the development of two component apatitic cements which exhibit improved storage stability. Such cements would provide the user with simple mixing regimens. In addition, significant reaction between the acidic and basic sources in the dry component of the cement would not occur before the dry component is combined with the lubricant. Thus, the cements could be stored for extended periods of time prior to use.

3. Relevant Literature

U.S. Pat. Nos. 4,888,610; 5,053,212; 5,129,905; and 5,178,845 describe various calcium phosphate cement compositions and methods for their production.

TenHuisen, "The Formation of Biocomposites at Physiological Temperature," Masters Thesis, The Pennsylvania State University Graduate School College of Earth and Mineral Sciences, August 1992, describes the formation of an intimate mixture of tetracalcium phosphate and monocalcium phosphate monohydrate by blending in a nonaqueous solvent.

TenHuisen and Brown, Journal of Biomedical Materials Research (1994) 28:27–33 describe the milling of tetracalcium phosphate with anhydrous dicalcium phosphate.

Lerner et al., Journal of Crystal Growth (1989) 97:725–730 describe rapid apatite formation from ethanol/water solutions.

SUMMARY OF THE INVENTION

Storage stable, two component apatitic cement compositions and methods for their production are provided. The dry component of the subject cement compositions comprise basic calcium source particles partially coated with a partially neutralized acidic calcium phosphate. The dry component of the subject compositions may be produced through mechanical mixing of an acidic phosphate source with a basic calcium particle source in the presence of a liquid phase, during which time reaction occurs between the two sources. Neutralization of the acidic phosphate source is stopped prior to completion through removal of available water. The resultant basic calcium source particles partially coated with a partially neutralized acidic calcium phosphate are storage stable and, when combined with a lubricant, form a rapidly setting apatitic product.

DESCRIPTION OF THE SPECIFIC EMBODIMENTS

Storage stable, two component apatitic cement compositions, as well as methods for their production, are provided. The cement compositions comprise as the dry component basic calcium source particles partially coated with a partially neutralized acidic calcium phosphate. The dry component of the subject compositions is prepared by combining basic calcium source particles with a dissolved acidic phosphate source in at least a partially aqueous medium, whereby the particles become partially coated with a partially neutralized acidic calcium phosphate. Prior to complete neutralization of the acidic phosphate source, the neutralization reaction is stopped through removal of the available water. In a first mode, the dry component of the subject cement compositions may be produced by mechanically mixing an acidic phosphate source with basic calcium source particles in the presence of an aqueous solvent and then stopping the reaction between the acid and base at a point prior to completion. The reaction between the acid and base is stopped prior to completion by removing substantially all of the free water from the reaction mixture. Alternatively, the dry component may be produced by combining a phosphoric acid solution with a basic calcium source particle slurry under conditions where partially neutralized acidic calcium phosphate precipitates on the surfaces of the basic calcium source particles. As in the first mode, the reaction is terminated by removal of the water from the reaction mixture.

Removal of water from the reaction mixture includes the situation where water is present in the reaction mixture in a limiting amount, such that neutralization of the acidic phosphate source is stopped when all available water is used in the neutralization reaction. To the resultant solids, additional calcium and/or phosphate sources, as well as additional modifying agents, may be added to produce the final dry component of the apatitic cement composition. Upon addition of a lubricant to this dry component, bone-like compositions or products are obtained, e.g. hydroxyapatite. In describing the subject invention further, the subject cement compositions will be discussed first, followed by a discussion of the alternative methods available for producing the subject cements.

The calcium to phosphate ratio of the subject two component cements may vary considerably depending on the particular apatitic product which is to be produced from the cement. Generally, the ratio of calcium to phosphate in the subject cement compositions will be greater than 1.0, usually ranging from 1.0 to 2.5. Where monetite and brushite are the desired calcium phosphate products, a cement with a calcium to phosphate ratio of 1.0 is preferred. Where octacalcium phosphate is the desired product, a cement with a calcium to phosphate ratio of 1.33 is desired. Where hydroxyapatite or dahllite (a carbonated form of hydroxyapatite) are the desired products, a cement with a calcium to phosphate ratio ranging from 1.33 to 2.0 is preferred, with a ratio around 1.67 being more preferred.

The basic calcium source found in the dry component of subject apatitic cement compositions may be any one of a variety of basic calcium sources. Basic calcium sources are known by those skilled in the art as calcium phosphates which, when added to water, raise the pH of the water to a value above 7. In general, the basic calcium sources should be more soluble than hydroxyapatite in water at pH 7. Illustrative basic calcium sources include $CaCO_3$ and basic calcium phosphates. Basic calcium phosphates that may find use in the subject invention will be those that have a calcium to phosphate ratio greater than 1.33, and include tricalcium phosphate, both $\alpha$ and $\beta$ forms, octacalcium phosphate, tetracalcium phosphate, as well as amorphous calcium phosphates having analogous properties, and will preferably be $\alpha$-tricalcium phosphate. The basic calcium source will be present in the dry component of the subject apatitic cement compositions in amounts of up to about 92% by dry weight, usually ranging from about 70 to 90% by dry weight, more usually ranging from about 80 to 90%

The basic calcium source particles found in the dry component of the subject apatitic cements will be at least partially coated with a partially neutralized acidic calcium phosphate. The proportion of the particle surface that is coated with the partially neutralized acidic calcium phosphate will be dependent on the calcium source particle size, with larger particles having a greater proportion of their surfaces coated with the acidic calcium phosphate. The proportion of the surface area of the basic calcium source particles which is coated will, on average, be less than about 40%, usually less than about 20%, and more usually less than about 10%.

The partially neutralized acidic calcium phosphate which partially coats the basic calcium source particles in the subject cement will be storage stable, i.e. not readily react with the other reactants present in the dry component of the two component cement composition, and have a calcium to phosphate ratio of at least about 1.0. The partially neutralized acidic calcium phosphate coating will be less hygroscopic and exhibit a higher thermal stability than orthophosphoric acid. Exemplary partially neutralized acidic calcium phosphates include monobasic calcium phosphate anhydrous (MCPA), monobasic calcium phosphate monohydrate (MCPM), dibasic calcium phosphate anhydrous (DCPA) and dibasic calcium phosphate dihydrate (DCPD). The coating of the basic calcium source particles may be homogeneous or heterogeneous with respect to the acidic calcium phosphate.

In addition to the basic calcium source particles at least partially coated with a partially neutralized acidic calcium phosphate, the dry component of the subject apatitic cement compositions may comprise additional agents which influence the characteristics of the apatitic product which is produced from the apatitic cement, such as calcium and or phosphate sources, polymers, proteins, and the like. When these additional calcium and/or phosphate sources are included, they may serve to modify the ratio of calcium to phosphate in the cement to provide an apatitic cement composition with a desired calcium to phosphate ratio, as described above. For example, where a cement composition having a calcium to phosphate ratio found in hydroxyapatite is desired, additional calcium sources may be included in the cement to raise the overall calcium to phosphate ratio to 1.67. Further, the additional calcium source may serve in a neutralizing capacity. The additional calcium and/or phosphate sources should be stable in the dry cement composition, i.e. they should not readily react with the other dry reactants in the cement composition. Additional phosphate sources, if included in the dry component, will be present in trace amounts. Additional calcium sources, if present in the cement composition, will be present in amounts of at least about 5% by dry weight, usually at least about 12 to 15% by dry weight and up to about 30% by dry weight of the apatitic cement composition. Exemplary additional calcium sources that may be present in the composition include calcium carbonate, calcium oxide, calcium hydroxide, calcium chloride, calcium acetate, calcium sulfate, and the like.

Other agents which may be present in the apatitic cement composition and modify the characteristics of the apatitic product produced from combination of the cement with a lubricant may also be present in the apatitic cement composition. Modification agents that may find use include surfactants, e.g. TWEEN®, sugars, small organic and inorganic molecules, e.g. salts, acrylic acids, e.g. polyacrylic and polycarboxylic acids, natural and synthetic polymers, proteins, and the like. Proteins of interest include collagen, particularly Type I collagen, fibrin, fibrinogen, keratin, tubulin, elastin, osteonectin, sialoproteins (BSP), $\alpha$-2HS-glycoproteins, bone-Gla-protein (BGP), matfix-Gla-protein, bone phosphoglycoprotein, bone phosphoprotein, bone proteoglycan, proteolipids, bone-morphogenetic proteins, emilage induction factor, platelet derived growth factor, skeletal growth factor, insulin growth factor, fibroblast growth factor, colony stimulating factor, and the like.

In some compositions, organic/inorganic matrices, such as the ones described in U.S. Pat. No. 5,231,169, the disclosure of which is herein incorporated by reference, may be included in the cement composition. These organic/inorganic matrices will typically comprise an organic matrix source within which crystals of acidic phosphate sources or basic calcium sources, as described above, have been precipitated. For example, collagen matrices can be included in the cement composition, where acidic phosphate sources and basic calcium sources are precipitated within the collagen fibrils. Methods of producing these organic/inorganic matrices are described below.

The dry component and a lubricant make up the subject two component cement compositions. Lubricants which may be included with the dry component are described in U.S. Pat. No. 5,129,905, the disclosure of which is herein incorporated by reference. The subject apatitic cements having been described, methods for making the dry component of the subject cements will now be discussed in greater detail.

In a first mode for producing the dry component of the apatitic cement compositions of the subject invention, an acidic phosphate particulate source is intimately, mechanically mixed with basic calcium source particles in the presence of a liquid phase, where the liquid phase is an aqueous solvent, to provide for reaction between the acid and the base. At a point prior to completion of the reaction between the acid and base, the reaction is stopped by removing substantially all of the free water from the reaction mixture. The resultant solids are then combined with any additional calcium, phosphate sources, as well as additional agents, to produce the final dry component of the apatitic cement composition.

Acidic phosphate particulate sources that find use in this first mode may or may not include calcium. Thus, orthophosphoric acid or acidic calcium phosphate sources may be employed. Exemplary acidic calcium phosphate sources include MCPM, MCPA, DCPD and DCPA. Pyrophosphates may also find use.

One or more basic calcium sources may be used in the first method, where at least one of the basic calcium sources will be the particle source which is partially coated with the partially neutralized acidic phosphate. The basic calcium sources which are not to be coated with the acidic calcium phosphate will typically be soluble in the aqueous solvent and react with the acidic phosphate source in the partial reaction, e.g. as a neutralizing agent, thereby influencing the nature of the partially neutralized acidic calcium phosphate that coats the basic calcium phosphate. Additional basic calcium sources include calcium carbonate, calcium oxide, calcium hydroxide and the like.

The amounts of acidic phosphate source and basic calcium source particles which are intimately, mechanically mixed into a reaction mixture will vary depending on the composition of the dry component of to be produced. The particle sizes of the dry reactants will range from about 0.1 to 150 μm, usually from about 0.1 to 40 μm. The weight ratio of the acidic phosphate reactant to the basic calcium source particle reactant in the reaction mixture will range from about 0.1 to 50%, usually from about 0.1 to 30%, and more usually from about 0.1 to 16%.

In the first mode, the dry ingredients are first mechanically mixed in the absence of a liquid phase to yield an intimate mixture. By intimate is meant that the acid and base reactants, as well as any additional reactants present in the reaction mixture, are brought into close proximity to one another by the mixing means. Mixing of the reactants in the absence of solvent may occur over a period of days, but will typically be less than a day, more typically less than a few hours, and frequently less than 0.5 hours.

Mechanical mixing of the acidic phosphate and basic calcium sources may be accomplished using any convenient means. Suitable mixing techniques include ball milling, Brabender mixing, ultrasonic mixing, mixing with a mortar & pestle, rolling between one or two rollers in a flexible container, and the like. Further, milling equipment may be employed to achieve the mechanical mixture of components. Suitable milling equipment includes ball mills, planetary mills, centrifugal mills, mechanofusion systems, air pulverizers, jet mills, vibratory mills, colloid mills, attritor mills, disc mills, ultrasonic milles, blenders and the like. The equipment elements which contact the milled reactants should be stable and inert under milling conditions. Exemplary materials for the mixing elements include alumina, zirconia, tungsten carbide, boron carbide, hard synthetic plastics, and the like.

Typically, the acidic and basic sources will be mechanically mixed for a sufficient period of time to provide a composition having a desired particle size range, where the desired particle size range typically ranges from 0.1 to 140 μm preferably 0.1 to 10 μm. Mixing prior to the addition of the aqueous solvent provides a homogenous distribution of the reactants prior to addition of the solvent and breaks up any agglomeration that may be present.

A liquid phase is then added to the mixture and the mixing is continued in a wet mixing phase. Liquids used in the mechanical mixing will be aqueous and may or may not include additional solutes. Thus, suitable solvents include water, preferably purified, deionized water. Additional solutes include alcohols, $Na_2HPO_4$, $Na_2CO_3$, NaCl, and the like. In addition to the aqueous solvents, the total solvent may also include non-aqueous, polar or non-polar solvents. The solvent will typically be added in sufficient volume to achieve a liquid to solid ratio of 0.15 to 1.0, usually 0.3 to 0.6.

The components will be mixed for a sufficient period of time to achieve the desired amount of reaction between the acidic and basic sources. The desired amount of reaction will usually be reached at some point prior to completion of the reaction, where completion of reaction refers to the complete neutralization of the acidic phosphate source under the conditions of the particular reactants in the reaction mixture, where water is not a limiting reactant. Typically, neutralization of the acidic phosphate source will proceed at most to 50% of completion, usually proceeding no more than 20% of completion and more usually no more than 10% of completion. After both dry mixing and mixing in the presence of a solvent are complete, the resultant reaction mixture may optionally be allowed to set for a period of time.

Once the desired amount of reaction between the acidic and basic sources has progressed to the desired point, the reaction, i.e. neutralization of the acidic phosphate source, is stopped. The reaction between the acid and the base is stopped prior to completion by removing substantially all of the free water from the reaction mixture. Removing substantially all of the free water from the reaction mixture can be accomplished using any convenient means.

One means for removing substantially all of the free water from the reaction mixture is to combine the reaction mixture with an excess amount of a non-aqueous solvent. Typically, the ratio of non-aqueous solvent to mixture will range from about 1000 to 1, usually from about 100 to 1, and more usually from about 50 to 1. The solids are then separated from the remaining liquid using any convenient method, e.g. filtration, distillation, centrifuging and the like. The solids of the reaction mixture may be further separated from the remaining liquids by using forced air, elevated temperatures and other dehydration means.

Another means for removing substantially all of the free water from the wet reaction mixture is freeze drying. Any convenient means of freeze-drying may be employed. For example, the wet mixture may be frozen by placing the mixture in a liquid nitrogen bath. Once frozen, the frozen water may be removed by sublimation. Yet another means for removing substantially all of the water from the reaction mixture is critical point drying.

After stopping the reaction between the mixed reactants, the resultant solids will comprise basic calcium source particles partially coated with a partially neutralized acidic calcium phosphate. The resultant solids may be milled to break up any agglomeration and therefore obtain a composition having a desired particle size distribution. Milling may be accomplished through any of the mechanical mixing techniques described above. Generally, milling will continue until particles ranging in size from about 0.01 to 15 μm are obtained.

The final step in the preparation of the two component apatitic cement composition is to combine the solids with any additional agents, resulting in the final dry component of the two component cement composition. These additional agents, e.g. supplemental calcium and/or phosphate sources or other modifying agents, as described above, may be added to the solids using any convenient means.

In an alternative mode of preparing the dry component of the subject apatitic cement compositions, a dispersion or slurry of basic calcium phosphate particles is rapidly combined with a phosphoric acid source. Rapid combination of the slurry with the phosphoric acid source into a reaction mixture results in reaction of the phosphoric acid source with the basic calcium phosphate. As with the previous method, prior to completion of the reaction between the phosphoric acid source and the basic calcium phosphate, the reaction is stopped by removing substantially all of the free water from the solids. The resultant solids comprise particles of basic calcium sources partially coated with partially neutralized acidic calcium phosphate. As in the first mode, these solids are incorporated into the dry component of the subject two component apatitic cements.

In this second mode of forming the subject calcium phosphate cement compositions, the liquid phase of the reaction mixture will be prepared from a combination of an aqueous solvent and a non-aqueous solvent. Aqueous solvents that find use include water, deionized water, $Na_2HPO_4$ solutions and the like. Non-aqueous solvents that find use include anhydrous ethanol and methanol, as well as organic solvents, both polar and non-polar, such as alkanes, e.g. heptane and the like. The proportion of the liquid phase present in the reaction mixture which is an aqueous solvent, and thus the amount of water available for reaction with the reactants in the reaction mixture, will influence the particular type of partially neutralized acidic calcium phosphate that forms on the surface of the basic calcium phosphate particles. Where an aqueous solvent makes up a high proportion of the liquid phase in the reaction mixture, DCPD and DCPA will be the favored type of partially neutralized acidic calcium phosphate to form on the surface of the basic calcium phosphate particles upon reaction. As used here, high proportion means 30 to 100% of the liquid phase, usually 40 to 90% of the liquid phase of the reaction mixture. Alternatively, where a low proportion of the liquid phase in the reaction mixture is aqueous, MCPM and MCPA will be the favored type of acidic calcium phosphate which forms on the surface of the basic calcium phosphate particles. As used here, low proportion means 0 to 10% of the liquid phase, usually 1 to 5% of the liquid phase.

The basic calcium phosphate dispersion, or slurry, may be prepared by combining the basic calcium phosphate particles with an excess of an aqueous and/or non-aqueous solvent, as described above. Typically, the liquids to solids ratio present in the dispersion will range from about 1 to 20, usually 5 to 10. Additional calcium sources may be included in the dispersion which influence the type of acidic calcium phosphate that precipitates on the calcium phosphate particles, such as the formation of MCPM over DCPD. Additional calcium sources that may find use include calcium acetate, calcium carbonate, calcium chloride, calcium sulfate and the like. The dispersion will be made by agitating the basic calcium phosphate particles, and any additional calcium sources, in the liquid phase. Any convenient agitation means may be employed.

The phosphoric acid source which is rapidly combined with the basic calcium phosphate particle slurry will typically be a concentrated orthophosphoric acid source, typically being 75 to 100% phosphoric acid, usually about 85% phosphoric acid. Preparation of the phosphoric acid source will depend on the form in which it is combined with the basic calcium phosphate slurry in the reaction mixture. The phosphoric acid source may be in a form free of uncombined water, e.g. in crystalline form, or may be combined with a liquid. Where the phosphoric acid source is free of uncombined water, it may be milled under dry conditions to obtain a particulate composition. Where the phosphoric acid source is liquid, preparation will usually involve dissolving crystalline orthophosphoric acid in the liquid. The liquid may be an aqueous solvent, non-aqueous solvent, or mixture of an aqueous solvent and non-aqueous solvent.

In addition to the phosphoric acid source and the basic calcium phosphate slurry, additional reactants which influence the reaction in the reaction mixture may be included. Additional reactants of interest include reactants which enhance the acidity of the reaction mixture, such as hydrochloric acid and the like.

Following preparation of the basic calcium phosphate particle slurry and phosphoric acid source, the acid source and the slurry are rapidly combined into a reaction mixture with agitation to maintain a substantially uniform dispersion. Rapid mixing is desirable for efficiently coating the basic calcium phosphate particles with the partially neutralized acidic calcium phosphate. The reaction mixture will be agitated for a period of time ranging from about 15 to 60 min, and usually from about 10 to 30 min. The temperature of the reaction mixture may be set to influence the particular acidic calcium phosphate that precipitates. Typically, the temperature of the reaction mixture will range from 18° to 80° C., usually from 20° to 40° C.

Reaction between the acidic phosphate source and the basic calcium phosphate particle source will be stopped prior to completion, where completion has the same definition as in the first mode, i.e. complete neutralization of the acidic phosphate source under the given conditions, where water is not a limiting reactant. The reaction will be stopped at point less than about 50% completion, usually at a point less than about 20% completion, and preferably at a point less than 10% of completion.

Reaction between the acid and base reactants is stopped by removing substantially all of the water from the reaction mixture, resulting in an apatitic cement precursor composition. As with the previous method, the water may be removed from the reaction mixture by separating the solids from the liquid phase. Removal of substantially all of the water, as used herein, also includes the situation where water is present in the reaction mixture as a limiting reactant. Thus, when all of the water has reacted in the partial neutralization of the acidic phosphate source, the reaction will stop, yielding a partially neutralized acidic calcium phosphate coating on the basic calcium particles. Separation of the solids from the liquid phase may be accomplished using any convenient means, such as filtration, distillation, freeze drying, critical point drying and the like. In addition, as described above, the solids may be combined with an excess volume of a non-aqueous liquid. The solids may additionally be dried at room temperature, or preferably, at elevated temperatures ranging from 40° to 80° C., preferably 70° to 75° C.. Drying times will range from about 2 to 72 hours, usually about 8 to 16 hours.

As in the first mode, the resultant solids will comprise basic calcium source particles partially coated with a partially neutralized acidic calcium phosphate. These solids are then combined with any additional agents to make the dry component of the two component cement composition.

The resultant two component cement compositions of the subject invention may be used promptly after manufacture, but will typically be stored for use at a later time. Generally, the subject cements will be stored in a substantially water free environment. Storage means may include air tight containers, air tight foil pouches, desiccated chambers, and the like. Storage times may range from as few as a couple of days to as long as several months, or longer.

In using the two component apatitic cements to produce a uniformly apatitic product, e.g. during a bone repair operation, the lubricant will be added to the dry component and the resultant paste allowed to set. The lubricant will conveniently be an aqueous physiologically acceptable lubricant, e.g. sterile water. The water which is used will be substantially pure, such as double distilled, deionized or the equivalent thereof. Additional solutes may be present in the lubricant. Phosphate and/or carbonate sources may be included in the lubricant, such as phosphate salts.

The amount of lubricant used is determined based on consistency of the paste, as well as rate of strength attainment and other functional characteristics. The amount of lubricant will generally be from about 15 to 70, more usually from about 25 to 45 weight percent of the entire apatitic cement composition. Preferably, lower amounts of water are used to provide for higher compressive strength and accompanying mechanical properties. The amount of water which is used may be calculated in relation to the amount of water which is formed by further reaction of the dry ingredients in the apatitic cement composition, so that in referring to the total amount of lubricant, this will include the water produced by the further reaction, as well as the water added to the mixture.

The apatitic cement composition and the lubricant are combined and thoroughly mixed to achieve a substantially uniform dispersion of the cement in the lubricant. Mixing may be accomplished by kneading, rolling, sonicating, or the like. During the mixing, any gas which is formed should be released. After mixing, the resultant moldable paste may be shaped into any appropriate form, to form a preformed object for use in bone repair. Mixing the cement with the lubricant lasts for a relatively short period of time, usually not less than about 0.5 minutes and not more than about 5 minutes, usually not more than about 3 minutes. Where the product is to be introduced in situ, e.g. during a bone repair operation, it may be injected into the appropriate site, using a syringe or catheter or other suitable introduction means, or packed in by other means, as appropriate. The injected paste is then allowed to set into a solid mass, whereby the bone is repaired at the bone repair site.

The moldable paste will be allowed to set, during which time crystals grow and the product becomes a single integral mass. While the apatitic product may set into a hard product almost immediately, usually the setting process should take at least about 2 min, usually about 8 min and not more than about 40 min, usually not more than about 15 min. Alternatively, where the product has been introduced at a site where it is to be retained, the material will naturally harden over time.

The following examples are offered by way of illustration and not by way of limitation.

EXPERIMENTAL

Example 1. Apatitic Cement of Tetracalcium Phosphate Partially Coated with DCPD 2.46 g MCPM was mixed with 12.54 g tetracalcium phosphate and 6.0 g deionized water in a mortar and pestle. The ratio of liquids to solids in the mixture was 0.40 and the calcium to phosphate ratio in the mixture was 1.67:1. The liquids and solids were mixed with the mortar and pestle for 3 min. The mixture was then allowed to set for 1 hr in a humidifier at 37° C. and 98% humidity.

The resultant solid was ground with a mortar and pestle for 5.0 min to obtain a powdery composition. The powder was then combined with 50 ml acetone for 5.0 min. The excess acetone was poured off and the remaining solids were allowed to dry at room temperature. The solids were milled with a mortar and pestle for 2.0 min to break up any agglomeration.

15 g of the resultant cement was then milled with 6.0 g of deionized water in a mortar and pestle, in a liquid to solid ratio of .40, for 3.0 min. The cement set in 4 minutes and had a compression strength of 5 MPa.

Example 2. Apatitic Cements from Partial Reaction of MCPM, $\alpha$-$C_3P$ and Calcite A. 0.493 g MCPM was mixed with 12.65 g $\alpha$-$C_3P$ and 1.85 g calcite in a glass mortar and pestle for 30 sec. The dry mix was milled for 1.5 min in the presence of 7.2 g deionized $H_2O$, in a liquid to solid ratio of 0.48. The wet milled composition was removed from the mortar and placed into centrifuge tubes. The centrifuge tubes were plunged into a liquid nitrogen bath. Once frozen, the tubes were placed in a lyophilizer overnight. The resultant cement was crushed in a mortar and pestle to break up any agglomeration. The cement comprised DCPD, $\alpha$-$C_3P$ and calcite.

1. 15 g of the cement produced in 2.A. was rehydrated with 6.6 g deionized $H_2O$, in a liquid to solid ratio of 0.44, and mixed in a mortar and pestle for 1 min. The cement set in less than 9 min and had a compression strength of 57 MPa, as determined using a modified American Standard Testing Methods based on ASTM # F451 § 6.9, where the procedure was modified as follows: (a) the number of tested samples was increased to 7; (b) the test material was injected into the die; (c) the material in the die was fingerpacked and then submersed in serum where it was cured at 37° C. and 98% RH; and (d) the material was allowed to set for 24 hours, then polished and tested for compressive strength.

2. 15 g of the cement produced in 2.A. was rehydrated with 6.45 g 0.075 m $Na_2HPO_4$, in a liquid to solid ratio of 0.43, and mixed in a mortar and pestle for 1 min. The cement set in less than 9 min.

3. The cement produced in 2.A. was stored for 30 days in an air tight, foil pouch. The stored cement was then rehydrated with 6.6 g 0.075 m $Na_2HPO_4$, in a liquid to solid ratio of 0.44, and milled with a mortar and pestle for 1 min. The cement set in less than 8 min and had a compression strength of 48.5 MPa.

B. 0.493 g MCPM was mixed with 12.65 g α-$C_3P$ and 1.85 g calcite in a glass mortar and pestle for 30 sec. The dry mix was milled for 1.5 min in the presence of 7.2 g 0.075M $Na_2HPO_4$, where the liquid to solid ratio was 0.48. The wet milled composition was removed from the mortar and placed into centrifuge tubes. The centrifuge tubes were plunged into a liquid nitrogen bath. Once frozen, the tubes were placed in a lyophilizer overnight, resulting in a calcium phosphate cement. The cement was crushed in a mortar and pestle to remove any agglomeration. The cement comprised DCPD, α-$C_3P$ and calcite.

15 g of the resultant cement was rehydrated with 6.6 g deionized $H_2O$, in a liquid to solid ratio of 0.44, and milled in a mortar and pestle for 1 min. The cement set in less than 33 min and had a compression strength of 33 MPa.

Example 3. Apatitic Cement Produced from Tetracalcium Phosphate, Calcite and Orthophosphoric Acid (oPA)

11.54 g of tetracalcium phosphate and 1.4016 g calcite were mixed in a mortar and pestle for 15 sec. The resultant homogenous mixture was milled for 30–45 sec. with 2.058 g of crystalline oPA. 7.5 g of 0.1 m $Na_2HPO_4$ was added to the dry mixture, in a liquid to solid ratio of 0.50. The mixture was wet milled for 2.5 min.

The composition was then transferred from the mortar into a centrifuge tube. The tube was placed into a liquid nitrogen bath. The resultant frozen composition was lyophilized overnight. After lyophilization, the remaining solids were crushed using mortar and pestle to break up any agglomeration.

The cement was rehydrated with 6.6 g deionized water in a liquid to solid ratio of 0.44. The rehydrated cement set in less than 9 min.

Example 4. Apatitic Cement Comprising α-$C_3P$ Crystals Coated with DCPD 50 g attritor milled α-$C_3P$ was added to 250 ml of deionized water in a 500 ml beaker. 356 μl 85% oPA (EM Sciences) was added to 50 ml of deionized water in a beaker using a microtip dispenser. The α-$C_3P$ slurry and oPA solution were then stirred using stir bars for 10 min. The α-$C_3P$ slurry was rapidly poured into the oPA solution and continuously stirred for an additional 30 min. The resultant solids were then filtered from the deionized water and dried for 16 hrs at 70° C. The resultant cement was ground in a mortar and pestle to break up any agglomeration.

The cement was then analyzed using X-ray diffraction to determine the acidic and basic calcium phosphates present in the cement. Based on the X-ray diffraction analysis, it was concluded that the cement comprised an intimate mixture of acidic and basic calcium phosphates, where DCPD (the acidic calcium phosphate) partially coated the surfaces of α-$C_3P$ particles (the basic calcium phosphate).

13.336 g of this cement was combined with 1.658 g calcite. 7.5 g of deionized water was added to this dry mixture resulting in an overall liquid to solid ratio of 0.50. The cement set in less than 17 min.

Example 5. Apatitic Cement Comprising α-$C_3P$ Particles Coated with MCPM 1.0 g of 100% crystalline oPA is dissolved in 6.2 ml of deionized water in a glass beaker. This oPA solution is added to 200 ml of ethanol in a large glass beaker and stirred with a stir bar on a stir plate. 25.3 g of α-$C_3P$ and 0.807 g of calcium acetate ($Ca(CH_3COO)_2$) are added to a second beaker containing 200 ml ethanol and stirred on a stir plate to achieve a slurry. The α-$C_3P$ slurry is rapidly poured into the oPA solution and stirred for approximately 15 min. MCPM precipitates onto the surface of the α-$C_3P$.

13.14 grams of a cement comprising α-$C_3P$ particles coated with MCPM, as produced above, are combined with 1.85 grams of calcite in a mortar and pestle. 7.2 g of deionized water or phosphate containing solution is added to the cement. The cement is allowed to set.

Example 6. Apatitic Cements Comprising Collagen Fiber Matrices in which DCPD and Calcite have been Precipitated A. Precipitation of MCPM within Collagen Fibrils 5 grams of collagen is dispersed in 1 liter of acetic acid having a pH of 4. After the collagen is dispersed, 0.794 g $CaCO_3$ and 0.777 g $H3PO_4$ are dissolved in the solvent. The $CaCO_3$ and $H3PO_4$ react to form DCPD within the open spaces between the dispersed collagen fibrils. Reaction is allowed to proceed until no more $CaCO_3$ remains in the solvent. The resultant solids comprise collagen fibrils within which DCPD is crystallized, i.e. an acidic phosphate/organic matrix. The solids are filtered from the solvent and dried.

B. Precipitation of Calcite within Collagen Fibrils 5 grams of collagen is placed in 1 liter of 0.02M NaOH solution, pH 11–12. In the basic solution, the collagen fibrils swell. After the fibrils have swollen, 2.937 g of $CaCl_2.2H_2O$ and 2.117 g $Na_2CO_3$ are dissolved in the solvent. Reaction occurs between the $CaCl_2.2H_2O$ and $Na_2CO_3$, resulting in the precipitation of $CaCO_3$ within the swollen collagen fibrils. When reaction has run to completion, the solids are filtered from the solvent. The resultant solids comprise collagen fibrils within which $CaCO_3$ crystals have precipitated, i.e. an organic/basic calcium matrix.

C. Preparation of Apatitic Cement Comprising Collagen Matrices

To the apatitic cements prepared in any of the previous examples, appropriate amounts of the collagen/MCPM matrix prepared as in 6.A and the collagen/calcite matrix prepared in 6.B are added, as desired. The resultant apatitic cement comprises collagen fibrils in close contact with the acidic phosphate and basic calcium sources.

It is evident from the above that improved single component apatitic cement compositions and methods for their production are provided. The subject compositions, when combined with a lubricant, provide bone-like calcium phosphate products suitable for use in the treatment of broken or deteriorated bones. The subject compositions are stable and may be stored for extended periods of time prior to use.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for producing a dry component for a storage stable, two component apatitic cement composition, said method comprising:

mixing an acidic phosphate source with a basic calcium source in the presence of an aqueous solvent, whereby a reaction between said acidic phosphate source and basic calcium source occurs; and stopping the reaction between said acidic phosphate source and basic calcium source prior to completion by removing substantially all of the free water from said reaction mixture, resulting in solids substantially free of uncombined water;

whereby a dry component comprising said basic calcium source at least partially coated with a partially neutralized acidic calcium phosphate is produced.

2. The method according to claim 1, wherein said basic calcium source is a basic calcium phosphate.

3. The method according to claim 2, wherein said basic calcium phosphate is selected from the group consisting of tricalcium phosphate, tetracalcium phosphate and octacalcium phosphate.

4. The method according to claim 1, wherein said acidic phosphate source is selected from the group consisting of monobasic calcium phosphate monohydrate, monobasic calcium phosphate anhydrous, dibasic calcium phosphate anhydrous, dibasic calcium phosphate dihydrate and orthophosphoric acid.

5. The method according to claim 1, wherein 100% of said mixing occurs in the presence of said liquid phase.

6. A method for producing a dry component for a storage stable two component apatitic cement composition, said method comprising:

mixing an acidic phosphate source with tricalcium phosphate in the absence of a liquid phase, resulting in a dry mixture;

mixing said dry mixture in the presence of an aqueous solvent; and stopping the reaction between said acidic phosphate source and tricalcium phosphate prior to completion by removing substantially all of the free water from said reaction mixture;

whereby a dry component comprising tricalcium phosphate partially coated with a partially neutralized acidic calcium phosphate is produced.

7. A method for producing a dry component for a storage stable two component apatitic cement composition, said method comprising:

mixing a phosphoric acid source with tricalcium phosphate in the presence of an aqueous solvent, whereby a reaction between said phosphoric acid source and said tricalcium phosphate occurs; and stopping the reaction between said phosphoric acid source and tricalcium phosphate prior to completion by removing substantially all of the free water from said reaction mixture;

whereby a dry component comprising tricalcium phosphate at least partially coated with a partially neutralized acidic calcium phosphate is produced.

\* \* \* \* \*